US011253708B2

(12) United States Patent
Baade et al.

(10) Patent No.: US 11,253,708 B2
(45) Date of Patent: Feb. 22, 2022

(54) MACHINED FEATURES OF ENCLOSURES FOR IMPLANTABLE MEDICAL DEVICES

(71) Applicant: MEDTRONIC, INC., Minneapolis, MN (US)

(72) Inventors: Michael J. Baade, Otsego, MN (US); Steven T. Deininger, Blaine, MN (US); Katherine J. Bach, Arden Hills, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 126 days.

(21) Appl. No.: 16/413,457

(22) Filed: May 15, 2019

(65) Prior Publication Data

US 2019/0358459 A1 Nov. 28, 2019

Related U.S. Application Data

(60) Provisional application No. 62/675,816, filed on May 24, 2018.

(51) Int. Cl.
*A61N 1/375* (2006.01)
*A61N 1/372* (2006.01)
*A61N 1/378* (2006.01)

(52) U.S. Cl.
CPC ............ *A61N 1/375* (2013.01); *A61N 1/3787* (2013.01); *A61N 1/37223* (2013.01)

(58) Field of Classification Search
CPC .. A61N 1/375; A61N 1/37223; A61N 1/3787; A61N 1/3758
See application file for complete search history.

(56) References Cited

U.S. PATENT DOCUMENTS

| 3,808,478 A | 4/1974 | Winkler |
| 4,173,745 A | 11/1979 | Saunders et al. |

(Continued)

FOREIGN PATENT DOCUMENTS

| WO | 2008100319 | 8/2008 |
| WO | 2010117842 | 10/2010 |

OTHER PUBLICATIONS

Standard Specification for Stainless Steel Sheet and Strip for Surgical Implants:, ASTM, designation F56-82.
Titanium Ti-6A-4V (Grade 5) Annealed, ASM.

*Primary Examiner* — Joseph M Dietrich
*Assistant Examiner* — Michael T. Holtzclaw
(74) *Attorney, Agent, or Firm* — Withers & Keys, LLC

(57) ABSTRACT

Implantable medical devices include an enclosure that is constructed by machining of a material rather than by forming or stamping. The machining produces one or more internal features within the enclosure. These internal features may include shelves that may act as a stiffener and create separate compartments within the enclosure. These internal features may include contoured edges along the shelves to accommodate conductors and other structures that extend from one compartment to another. These features may include slots that are present in one or more locations, such as on a surface of one of the shelves. These internal features may also include standoffs that establish a gap between an internal component and the external wall of the enclosure. These internal features may also include different thicknesses in different areas of the enclosure, such as one wall thickness in one compartment and a different wall thickness in another compartment.

23 Claims, 10 Drawing Sheets

(56) References Cited

U.S. PATENT DOCUMENTS

| | | |
|---|---|---|
| 4,254,775 A | 3/1981 | Langer |
| 4,296,390 A | 10/1981 | Vanderheyden et al. |
| 4,514,782 A | 4/1985 | Sakamoto et al. |
| 4,995,389 A | 2/1991 | Harris |
| 5,032,692 A | 7/1991 | DeVolder |
| 5,040,091 A | 8/1991 | Yamaoka |
| 5,176,136 A | 1/1993 | Giele |
| 5,336,246 A | 8/1994 | Dantanarayana |
| 5,470,345 A | 11/1995 | Hassler et al. |
| 5,751,539 A | 5/1998 | Stevenson et al. |
| 5,905,627 A | 5/1999 | Brendal et al. |
| 6,083,640 A | 7/2000 | Lee et al. |
| 6,118,672 A | 9/2000 | Yamauchi et al. |
| 6,248,080 B1 | 6/2001 | Miesel et al. |
| 6,297,943 B1 | 10/2001 | Carson |
| 6,414,835 B1 | 7/2002 | Wolf et al. |
| 6,498,951 B1 | 12/2002 | Larson et al. |
| 6,529,103 B1 | 3/2003 | Brendal et al. |
| 6,566,978 B2 | 5/2003 | Stevenson et al. |
| 6,643,903 B2 | 11/2003 | Stevenson et al. |
| 6,658,296 B1 * | 12/2003 | Wong ............... A61N 1/375 607/37 |
| 6,660,116 B2 | 12/2003 | Wolf et al. |
| 6,721,602 B2 | 4/2004 | Engmark et al. |
| 6,765,779 B2 | 7/2004 | Stevenson et al. |
| 6,850,405 B1 | 2/2005 | Mileham et al. |
| 6,936,899 B2 | 8/2005 | Juengling |
| 6,987,428 B2 | 1/2006 | Marketkar et al. |
| 7,035,076 B1 | 4/2006 | Stevenson |
| 7,035,077 B2 | 4/2006 | Brendel |
| 7,113,387 B2 | 9/2006 | Stevenson et al. |
| 7,187,535 B1 | 3/2007 | Iyer |
| 7,236,829 B1 | 6/2007 | Farazi et al. |
| 7,242,982 B2 | 7/2007 | Singhal et al. |
| 7,260,434 B1 * | 8/2007 | Lim ............... A61N 1/3754 607/37 |
| 7,306,490 B1 | 12/2007 | Jeter |
| 7,317,946 B2 | 1/2008 | Twetan et al. |
| 7,363,090 B2 | 4/2008 | Halperin |
| 7,515,964 B1 | 4/2009 | Alexander |
| 7,590,450 B2 | 9/2009 | Iyer et al. |
| 7,594,828 B2 | 9/2009 | Alexander et al. |
| 7,630,768 B1 | 12/2009 | Coffed et al. |
| 7,668,597 B2 | 2/2010 | Engmark et al. |
| 7,693,576 B1 | 4/2010 | Lavie et al. |
| 7,725,177 B2 | 5/2010 | Iyer |
| 7,725,190 B2 | 5/2010 | Iyer et al. |
| 7,748,093 B2 | 7/2010 | Iyer et al. |
| 7,765,005 B2 | 7/2010 | Stevenson |
| 7,803,014 B2 | 9/2010 | Sprain et al. |
| 7,839,620 B2 | 11/2010 | Iyer et al. |
| 7,917,218 B2 | 3/2011 | Iyter et al. |
| 8,131,368 B2 | 3/2012 | Kast et al. |
| 8,154,846 B2 | 4/2012 | Fauer et al. |
| 8,494,649 B2 | 7/2013 | Stancer et al. |
| 8,593,816 B2 | 11/2013 | Iyer et al. |
| 8,604,341 B2 | 12/2013 | Barry et al. |
| 9,138,821 B2 | 9/2015 | Brosnan et al. |
| 9,259,591 B2 * | 2/2016 | Brown ............... A61N 1/375 |
| 9,511,236 B2 * | 12/2016 | Varady ............... B23K 26/206 |
| 9,572,993 B2 | 2/2017 | Deininger et al. |
| 9,597,518 B2 | 3/2017 | Deininger et al. |
| 10,286,218 B2 | 5/2019 | Deininger |
| 2002/0165588 A1 | 11/2002 | Fraley et al. |
| 2003/0139096 A1 | 7/2003 | Stevenson et al. |
| 2003/0163171 A1 | 8/2003 | Kast et al. |
| 2004/0176815 A1 | 9/2004 | Janzig et al. |
| 2004/0220627 A1 | 11/2004 | Crespi et al. |
| 2006/0015150 A1 | 1/2006 | Rusin et al. |
| 2007/0203530 A1 | 8/2007 | Hubing et al. |
| 2007/0248881 A1 | 10/2007 | Scott et al. |
| 2008/0033500 A1 | 2/2008 | Strother et al. |
| 2008/0246231 A1 | 10/2008 | Sjostedt et al. |
| 2010/0009512 A1 | 1/2010 | Fishburn |
| 2010/0177458 A1 | 7/2010 | Iyer |
| 2010/0274309 A1 * | 10/2010 | Knipfer ............... A61N 1/37518 607/36 |
| 2011/0029028 A1 | 2/2011 | Peters |
| 2012/0053646 A1 | 3/2012 | Brase et al. |
| 2012/0151758 A1 * | 6/2012 | Primavera ............ A61N 1/3758 29/761 |
| 2012/0193141 A1 | 8/2012 | Reisinger et al. |
| 2012/0203314 A1 | 8/2012 | Deininger |
| 2013/0150915 A1 * | 6/2013 | Kane ............... A61N 1/375 607/36 |
| 2014/0043739 A1 | 2/2014 | Deininger |
| 2014/0049924 A1 | 2/2014 | Deininger |
| 2015/0066113 A1 * | 3/2015 | Van Funderburk ............ A61N 1/37512 607/60 |
| 2016/0157371 A1 * | 6/2016 | Glynn ............... B22F 7/062 312/209 |
| 2016/0260938 A1 * | 9/2016 | Nielsen ............ H01M 10/4257 |
| 2017/0087358 A9 | 3/2017 | Deininger et al. |
| 2017/0087359 A9 | 3/2017 | Deininger et al. |
| 2018/0015290 A1 | 1/2018 | Deininger et al. |
| 2018/0272138 A1 * | 9/2018 | Tahmasian ............ A61N 1/3756 |
| 2020/0086117 A1 * | 3/2020 | Verzal ............... A61N 1/375 |
| 2020/0259151 A1 * | 8/2020 | Deininger ............ H01R 12/75 |

\* cited by examiner

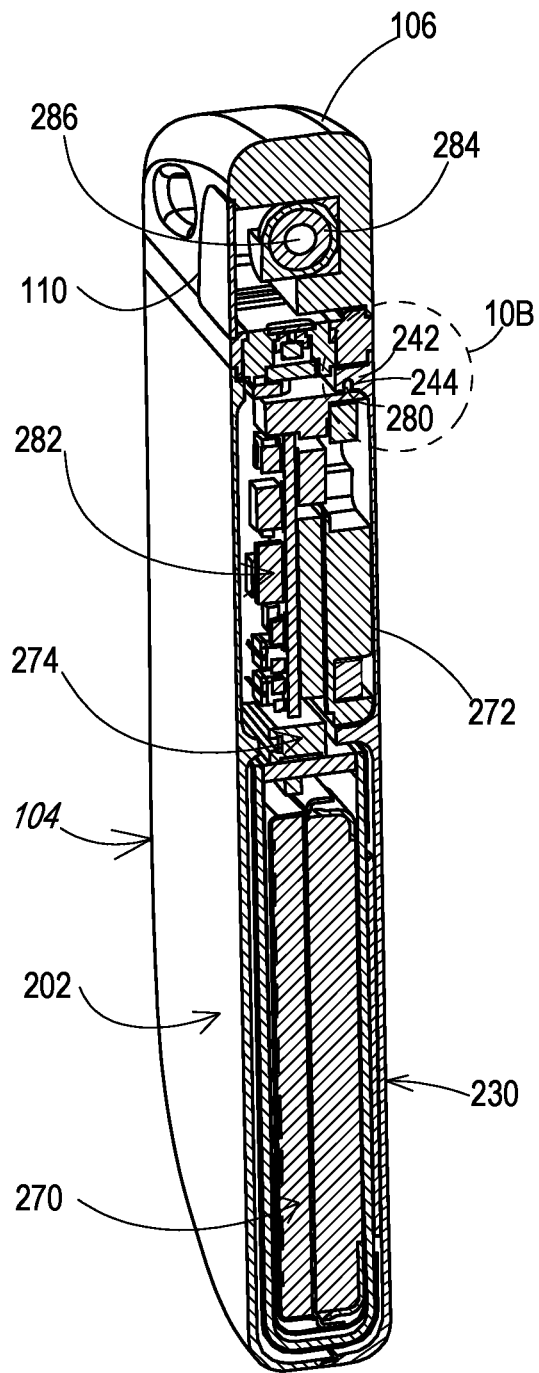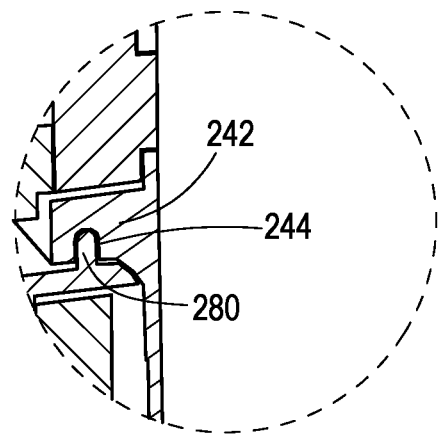
FIG. 10A
FIG. 10B

MACHINED FEATURES OF ENCLOSURES FOR IMPLANTABLE MEDICAL DEVICES

RELATED APPLICATIONS

This application claims priority to U.S. Provisional Application No. 62/675,816, filed on May 24, 2018.

TECHNICAL FIELD

Embodiments related to enclosures for implantable medical devices. More particularly, embodiments relate to machined features of such enclosures.

BACKGROUND

Implantable medical devices that provide stimulation and/or biological sensing therapy are typically constructed as an enclosure that houses electrical circuitry. The enclosure is typically constructed by a process such as stamping, hydroforming, and the like to form a sheet of biocompatible material into a desired shape. Often, the enclosure is formed of two halves that are formed, the electrical circuitry is installed, and the two halves are then welded together.

While forming an enclosure in this manner may produce a reliable device, there are limitations on the materials that can be used. For instance, certain biocompatible materials cannot reliably be formed, such as various grades of titanium that are too hard. This is particularly troublesome for implantable medical devices that utilize internal coils to provide wireless recharging. The harder grades of titanium allow for more efficient wireless recharging than many materials that may be stamped or otherwise formed into an enclosure.

One manner of overcoming the limitation on which materials may be used is to machine an enclosure from a block of material rather than using forming. Techniques such as electric discharge machining or milling may be used to produce the enclosure halves. While machining has produced enclosures of harder materials but of the same design as that of enclosures stamped or otherwise formed, limitations still persist. For instance, the enclosure design typically used with stamping or forming lacks internal features that assist in assembly and construction. Thus, a machined version of that same enclosure that uses a harder material still lacks those internal features.

SUMMARY

Embodiments address issues such as these by providing enclosures that are machined with internal features that aid in the assembly, construction, and/or operation of the implantable medical device. For example, a shelf may be machined into one or both opposing sidewalls of an enclosure to add stiffness to the wall and/or to create separate compartments on each side of the shelf, with the shelf supporting the fixation of items in each compartment. Fixation features may be included, such as having contours within a shelf that mate with contours of items located within the compartments to provide fixation. As another example, wall thickness may be machined so as to vary for a given wall of an enclosure, such as where one compartment has a relatively small thickness that improves telemetry and/or wireless recharging while another compartment formed by the same wall has a larger wall thickness to resist warping. Standoffs may be machined into the one or more walls to separate internal items from the internal wall surface, for instance, to better protect the internal items when enclosure halves are being welded together. Likewise, slots may be defined in interior features to receive ridges of internal items to provide for proper positioning and fixation.

Embodiments provide an implantable medical device that includes an enclosure forming a first compartment and a second compartment, the enclosure providing a shelf that separates the first compartment from the second compartment. The implantable medical device includes electrical circuitry located within the first compartment. The implantable medical device further includes a battery located within the second compartment, with electrical conductors passing from the battery to the electrical circuitry.

Embodiments provide an implantable medical device that includes an enclosure forming a first compartment and a second compartment. A first wall portion of the enclosure provides a surface of the first compartment, the first wall portion having a thickness, and a second wall portion of the enclosure provides a surface of the second compartment, the second wall portion having a thickness that is different than the thickness of the first wall. Electrical circuitry is located within the enclosure.

Embodiments provide an implantable medical device that includes an enclosure forming a wall, the wall defining at least one standoff. Electrical circuitry is present within the enclosure. A battery is located within the enclosure and electrically coupled to the circuitry, wherein the at least one standoff spaces the battery from the wall.

Embodiments provide an implantable medical device that includes an enclosure forming at least a first compartment. The enclosure defines a slot in the interior of the first compartment. A chassis is positioned within the first compartment and has a ridge, the ridge being positioned within the slot. Electrical circuitry is located within the chassis.

Embodiments provide a method of constructing an enclosure for a medical device. The method involves machining an enclosure from a material, the machining producing a shelf that separates the enclosure into a first compartment and a second compartment. The method further involves placing electrical circuitry within the first compartment and placing a battery within the second compartment, with electrical conductors passing from the battery to the electrical circuitry.

Embodiments provide a method of constructing an enclosure for a medical device that involves machining an enclosure from a material, the machining producing a first compartment and a second compartment where a first wall portion of the enclosure provides a surface of the first compartment. The first wall portion has a thickness. A second wall portion of the enclosure provides a surface of the second compartment, and the second wall portion has a thickness that is different than the thickness of the first wall portion. The method further involves placing electrical circuitry within the enclosure.

Embodiments provide a method of constructing an enclosure for a medical device. The method involves machining an enclosure from a material, the machining producing an enclosure forming a wall, the wall defining at least one standoff. The method further involves placing electrical circuitry within the enclosure and placing a battery within the enclosure that is electrically coupled to the circuitry. The at least one standoff spaces the battery from the wall.

Embodiments provide a method of constructing an enclosure for a medical device. The method involves machining an enclosure from a material, the machining producing an enclosure forming at least a first compartment, the enclosure defining a slot in the interior of the first compartment. The method further involves placing electrical circuitry within a chassis and placing the chassis within the first compartment. The chassis has a ridge, the ridge being positioned within the slot.

DESCRIPTION OF THE DRAWINGS

FIG. 10A shows a front cross-sectional perspective of the complete implantable medical device.

FIG. 10B shows an enlarged view of a slot and corresponding ridge of the complete implantable medical device.

DETAILED DESCRIPTION

Embodiments are disclosed herein that provide machined features within an enclosure of an implantable medical device. Examples of these features include shelves, fixation contours on the shelves and/or in other locations, standoffs along one or more walls, slots within the shelves and/or in other locations, and varying wall thicknesses. These features aid in one or more aspects of the implantable medical device such as facilitating the assembly of the internal components to the enclosure, establishing internal component fixation, providing overall device rigidity, improving efficiency of wireless operations, and protecting internal components during welding of enclosure shells.

Figure 1:
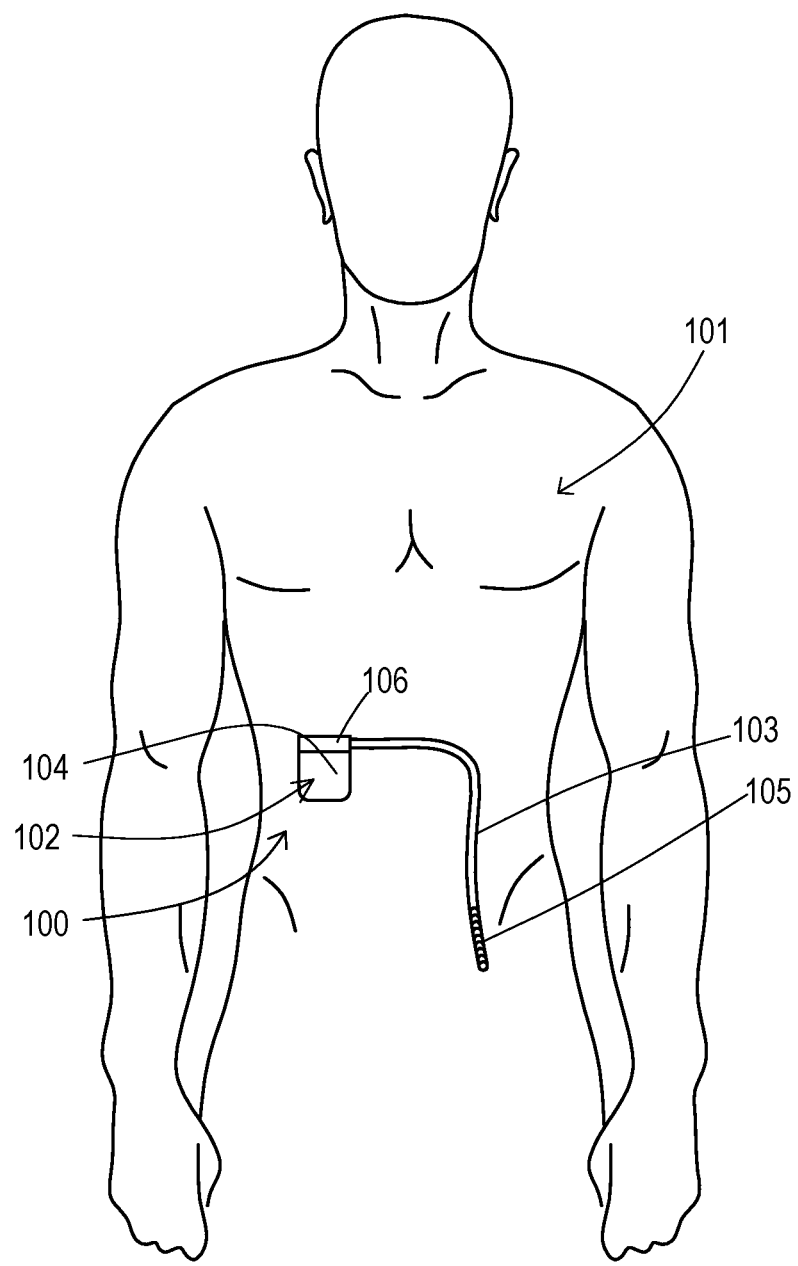
FIG. 1 shows an operational environment for embodiments of implantable medical devices.

FIG. 1 shows a medical system 100 that includes an embodiment of a medical device 102 and a medical lead 103. In this particular example, the medical system 100 and the individual elements including the medical device 102 and the medical lead 103 are each implantable. The medical lead 103 includes a proximal end that has been inserted into a bore of a header 106 of the medical device 102 that is mounted atop an enclosure 104 that may include various machined features discussed below. The distal end of the medical lead 103 includes electrodes 105 that are positioned at a target site where electrical stimulation therapy and/or sensing is to be provided.

A lead extension not shown in FIG. 1 may also be present where the proximal end of the lead extension is inserted into the medical device 102, with the lead 103 then being inserted into a connector block on a distal end of the lead extension. It will be understood that the specific implant and lead/lead extension location within a patient 101 as shown in FIG. 1 is to provide an example and that the embodiments of the medical system 100 apply to any device and lead location.

Figure 2:
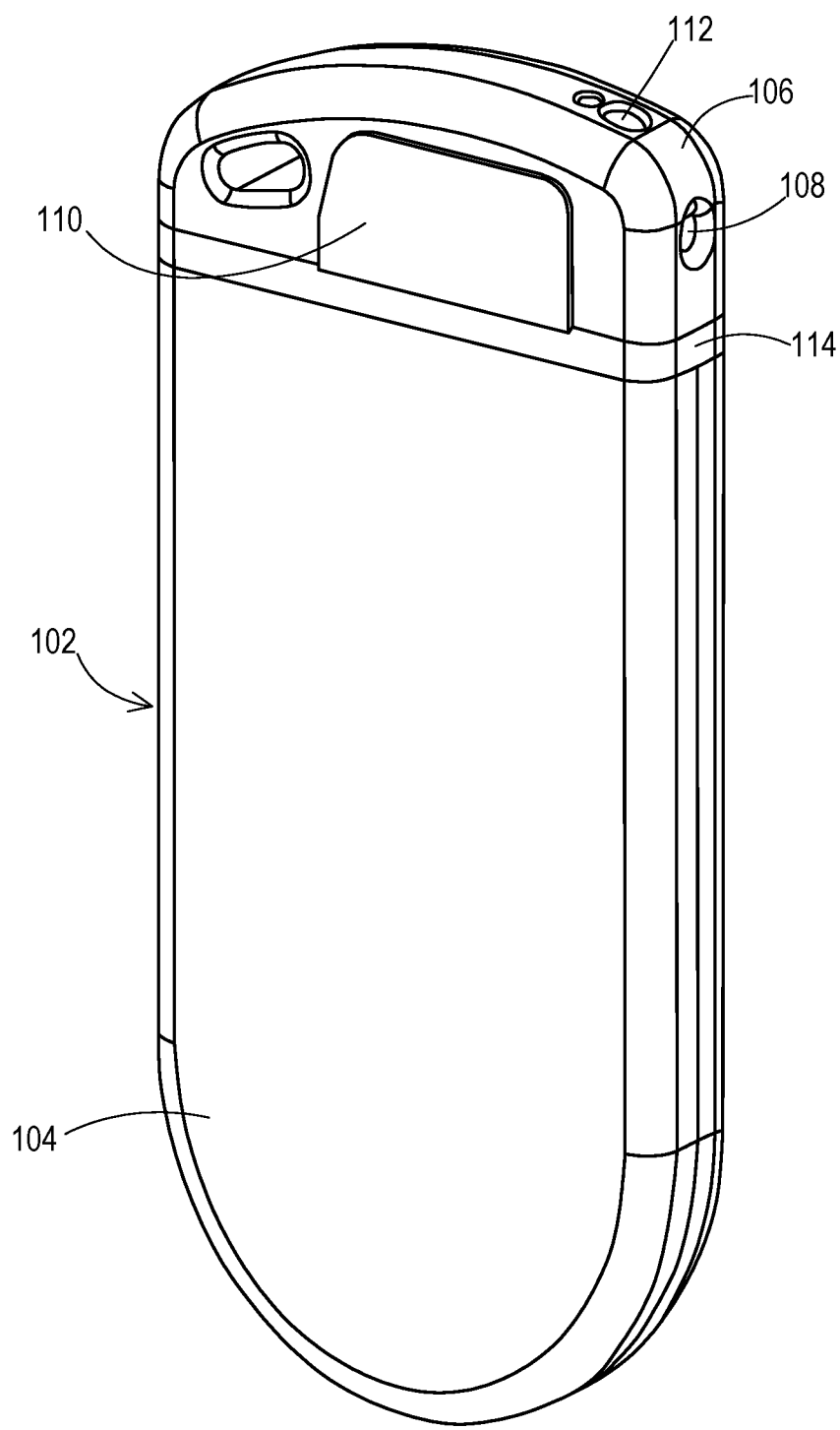
FIG. 2 shows a left side perspective of an embodiment of the implantable medical device including an enclosure and a header.
Figure 3:
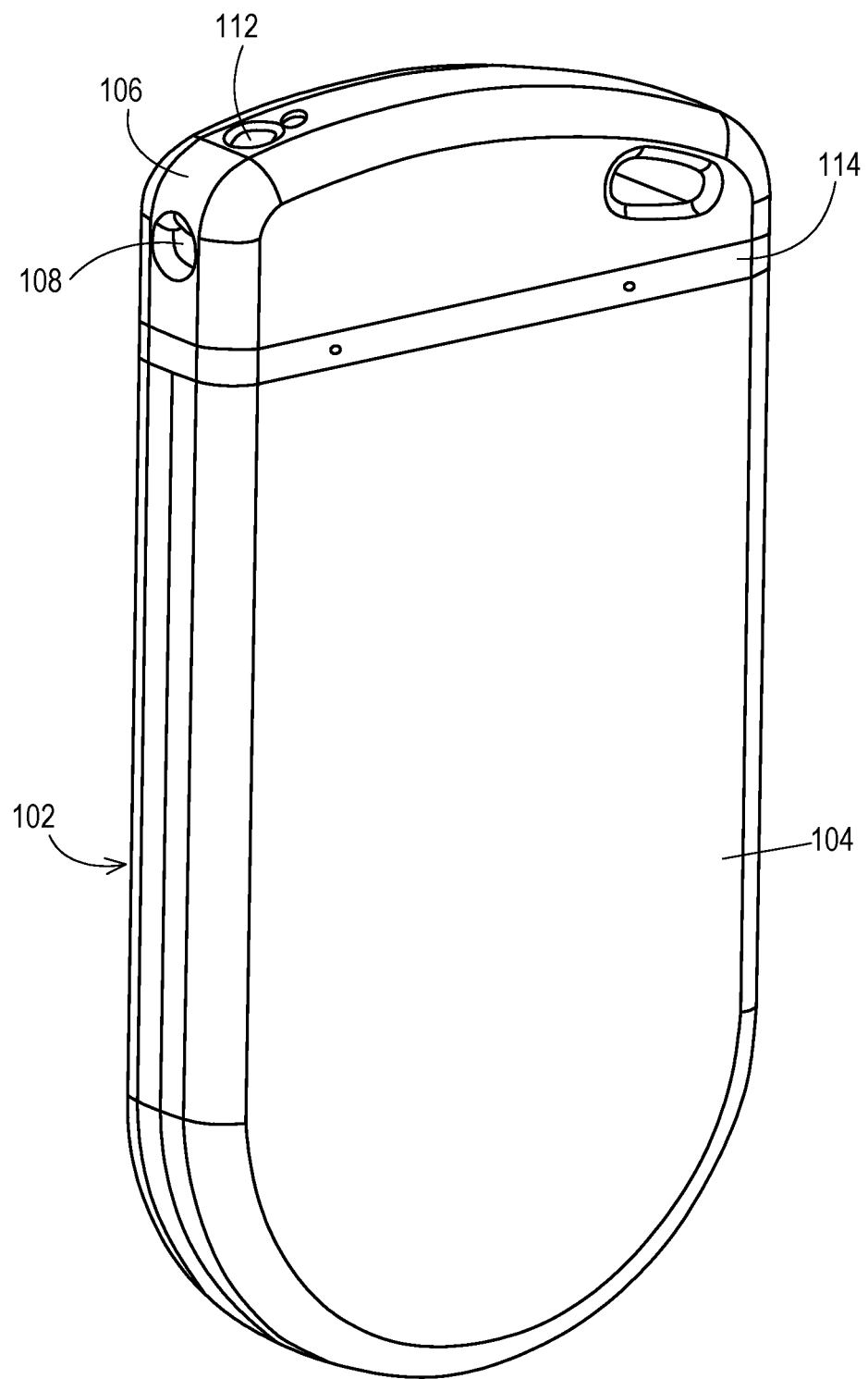
FIG. 3 shows a right side perspective of the embodiment of the implantable medical device including the enclosure and the header.

FIG. 2 provides a left side perspective view of one example of the medical device 102, and FIG. 3 provides a right side perspective view. The medical device 102 includes the enclosure 104 which houses electrical circuitry and may also house a battery that provides power to the electrical circuitry. The enclosure 104 may be machined into various shapes and sizes. The particular shape, size, and proportions as shown in these figures are for purposes of illustration and example, as different applications may call for the enclosure to have different shapes, sizes, and proportions than those shown. Because the enclosure 104 is machined, the material that is chosen may be a relatively hard biocompatible metal such as Titanium Grade 5, although many other materials are also possible such as Titanium Alloy 6Al-4V ELI, Titanium Ti-8Al-1Mo-1V and Titanium Grade 23.

In this example, a header 106 is mounted atop the enclosure 104. The header 106 includes a base 114 that is directly attached to the top of the enclosure 104. The base 114 may also be constructed of a biocompatible metal, and the enclosure 104 and the base 114 may be welded or otherwise bonded together. The remainder of the header 106 may also be a biocompatible metal and the enclosure 104, base 114, and header 106 may act as an electrical node for the stimulation therapy. Electrical connectors within the header 106 are electrically isolated from the header 106 by way of non-conductive filler material that surrounds the electrical connectors and any conductors passing from the electrical connectors through the base 114 and into the enclosure 104. A panel 110 may be present to cover an access hole within the header 106 where the access hole allows the introduction of electrical connectors and conductor pins during assembly. The panel 110 may then be welded in place to hermetically seal the header 106 which is then filled with non-conductive filler through a port hole.

During implantation, a proximal end of the lead 103 is introduced into the header 106 via a lead bore 108. Electrical contacts on the proximal end of the lead 103 connect to the electrical connectors fixed within the header 106. The header 106 may include a hole 112 that includes threads or a threaded insert where a set screw is positioned to allow tightening of the set screw onto an electrical contact of the lead 103. The set screw thereby fixes the position of the lead 103.

Figure 4:
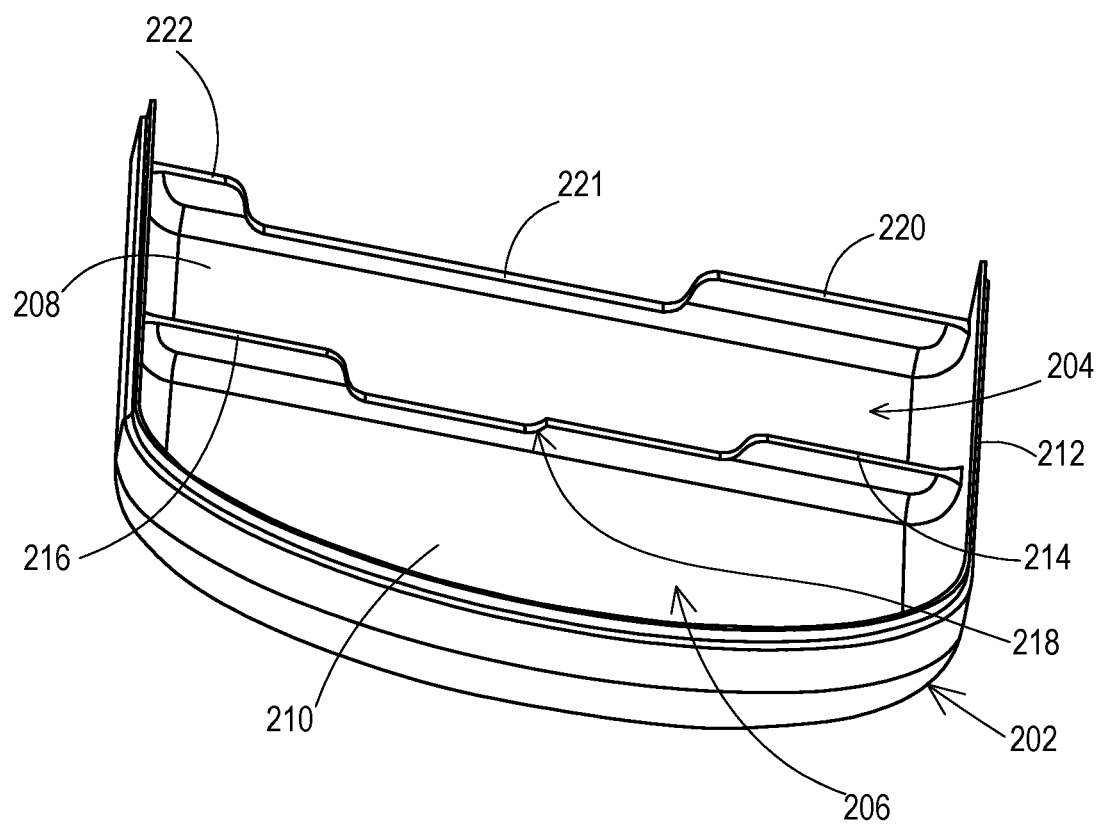
FIG. 4 shows an upward facing perspective of a first enclosure shell that provides the wall seen in the left side perspective of FIG. 2.
Figure 5:
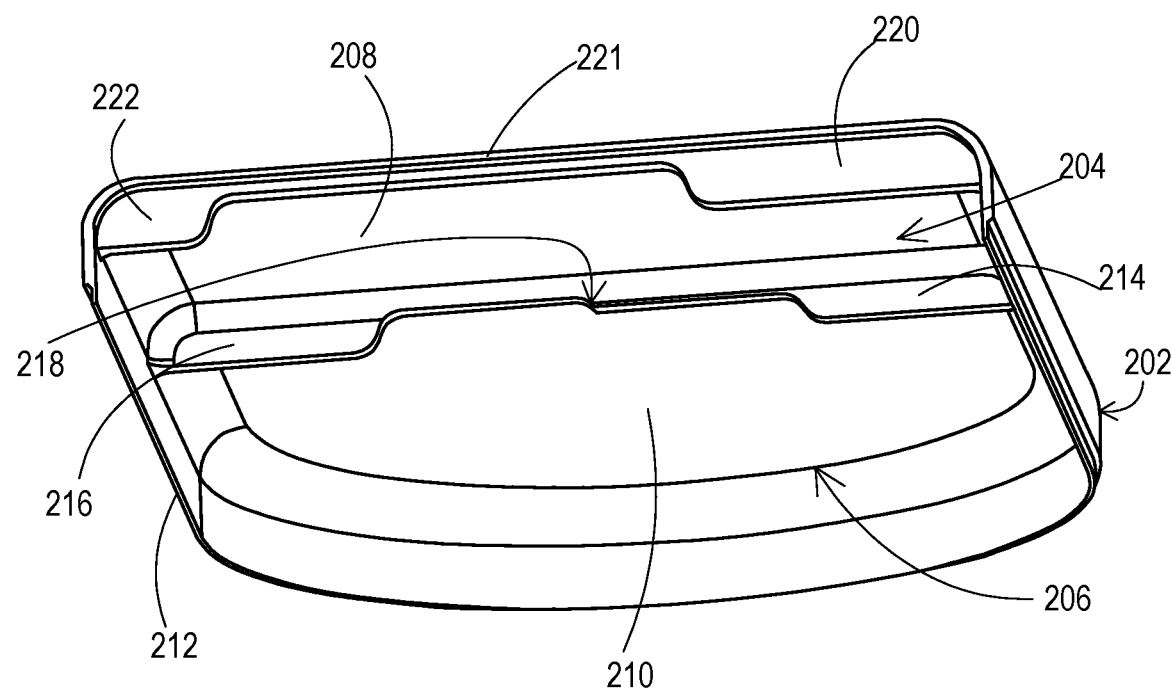
FIG. 5 shows a downward facing perspective of a first enclosure shell that provides the wall seen in the left side perspective of FIG. 2.

The enclosure 104 may be constructed of two portions that are independently machined and then welded together during assembly of the medical device 102. FIG. 4 shows an upward facing view and FIG. 5 shows a downward facing view of one portion 202 that provides the left side of the enclosure 104 as seen in FIG. 2. This portion 202 is machined to form a wall having a top wall portion 208 and a bottom wall portion 210. The wall transitions around the periphery to become a boundary wall and edge 212.

Machining the portion 202 allows for internal features to be included. One example is the intermediate shelf 214, 216. This intermediate shelf 214, 216 divides the portion 202 into an upper compartment 204 and a lower compartment 206. The top wall portion 208 further creates the upper compartment 204 while the bottom wall portion 210 further creates the lower compartment 206. The shelf 214, 216 provides a structure that allows internal components to be secured in place in each of the compartments 204, 206. As discussed below, in one example electrical circuitry may be contained in the upper compartment 204 while a battery that powers the electrical circuitry may be contained in the lower compartment 206.

One or more additional shelves may also be present, such as a top shelf 220, 222. This top shelf 220, 222 provides a separation between the top compartment 204 and the bottom of the base 114 of the header 106.

Each of the shelves 214, 216 and 220, 222 also acts as a stiffener to the enclosure portion 202 and to the full enclosure 104 upon portion 202 and portion 230 (shown in FIGS. 6 and 7) being joined together during assembly of the medical device 102. The stiffener aids in resisting the enclosure walls from being twisted, warped, pressed inward or outward, or from otherwise being distorted from the original shape.

Each of the shelves 214, 216 and 220, 222 may include a contoured edge 218, 221 that reduces the size of the shelf in the contoured area. The contoured edge 218, 221 and reduced size of the shelf in the contoured area may be present to accommodate additional internal features that transition from one of the compartments 204, 206. For instance, the contoured edge 218 accommodates a structure that channels conductors from the battery in the lower compartment 206 to the electrical circuitry in the upper compartment 204. The contoured edge 221 accommodates a structure that channels conductors from the electrical connectors in the header 106 to the electrical circuitry in the upper compartment 204.

Figure 6:
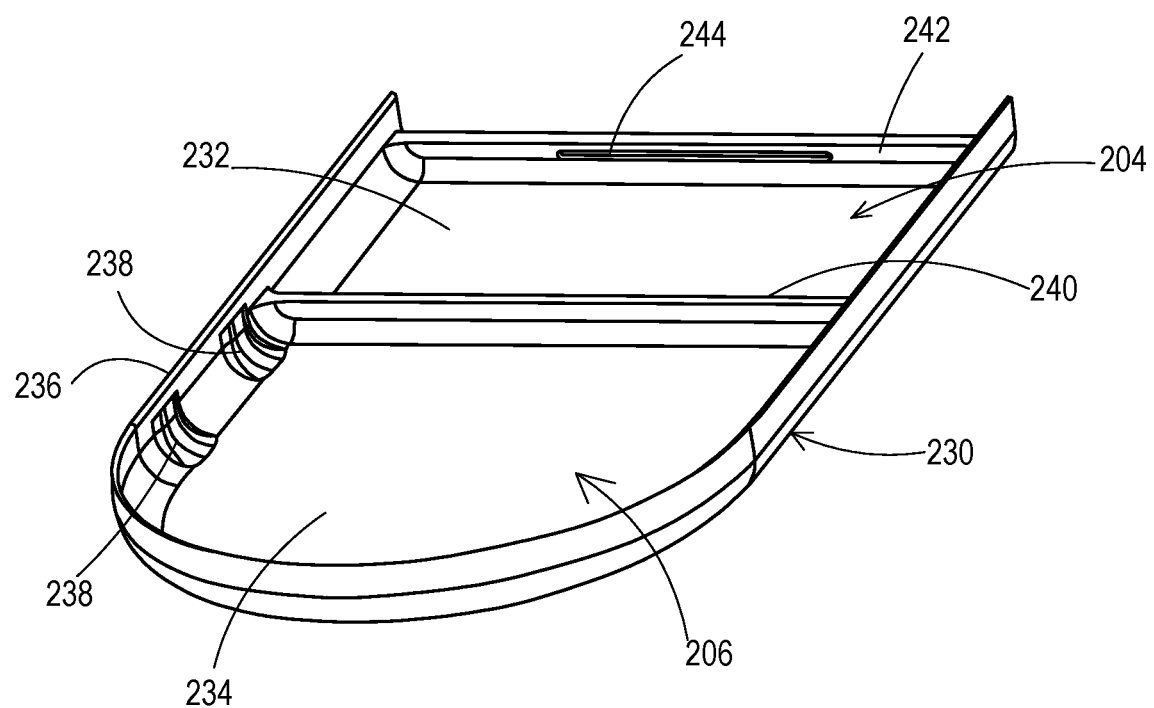
FIG. 6 shows an upward facing perspective of a second enclosure shell that provides the wall seen in the right side perspective of FIG. 3.
Figure 7:
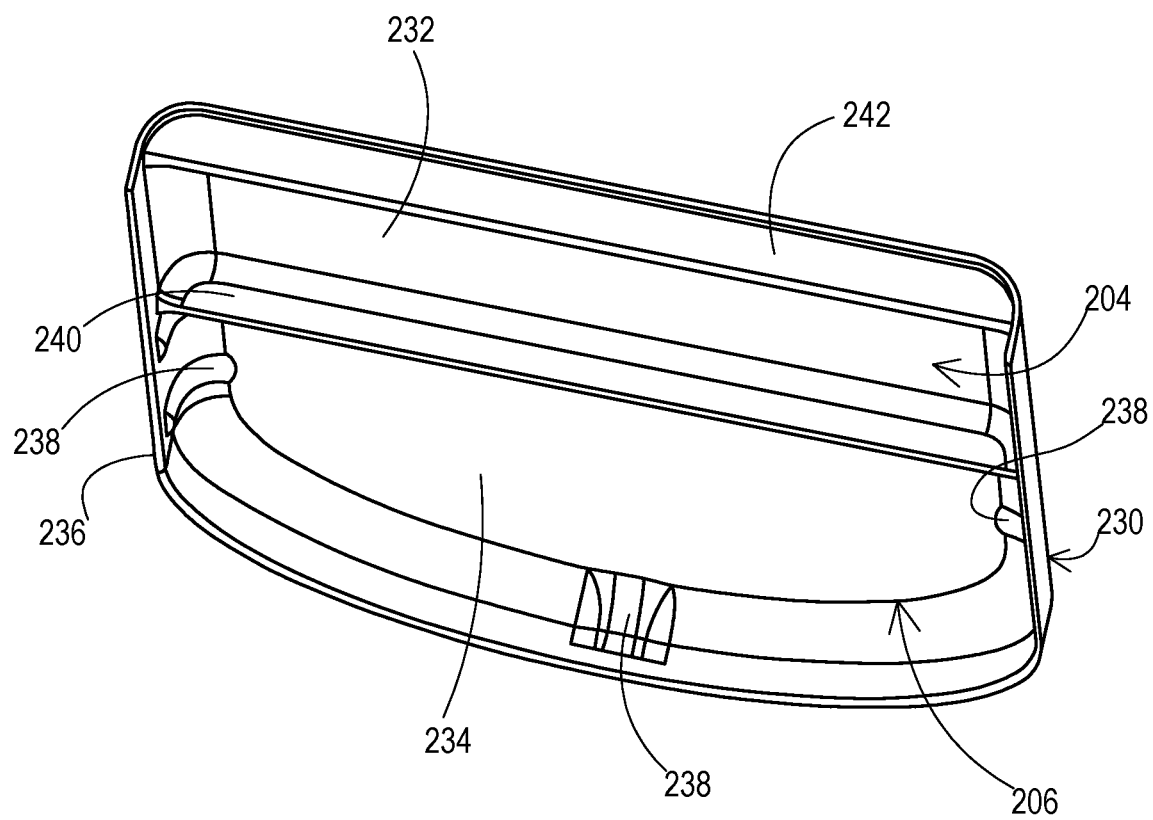
FIG. 7 shows a downward facing perspective of a second enclosure shell that provides the wall seen in the right side perspective of FIG. 3.

An example of the second portion 230 of the enclosure's two portions that are independently machined and then welded together during assembly is shown in FIGS. 6 and 7. FIG. 6 shows an upward facing view and FIG. 7 shows a downward facing view of the portion 230 that provides the right side of the enclosure 104 as seen in FIG. 3. This portion 230 is also machined to form a wall having a top wall portion 232 and a bottom wall portion 234. The wall transitions around the periphery to become a boundary wall and edge 236.

Machining the portion 230 allows for additional internal features to be included. One example is an intermediate shelf 240. This intermediate shelf 240 also divides the portion 230 into the upper compartment 204 and the lower compartment 206 discussed above in relation to FIGS. 4 and 5. The top wall portion 232 further creates the upper compartment 204 while the bottom wall portion 234 further creates the lower compartment 206. The shelf 240, along with the shelf 214, 216 of the portion 202 that becomes adjacent to the shelf 240 during assembly of the device 102, provides the structure that allows internal components to be secured in place in each of the compartments 204, 206.

One or more additional shelves may also be present, such as a top shelf 242. This top shelf 242, along with the top shelf 220, 222 of the portion 202, also provides a separation between the top compartment 204 and the bottom of the base 114 of the header 106. In this example, the top shelf 242 itself includes an additional internal feature, a slot 244 on the underside of the shelf 242, that is formed during machining of the portion 202. This slot 244 aids in the assembly and operation of the device 102 by receiving a ridge of an internal component, discussed in more detail below, during assembly to align and stabilize the position of the internal component.

Each of the shelves 240 and 242 also acts as a stiffener to the enclosure portion 230 and to the full enclosure 104 upon the portion 202 and portion 230 being joined together during assembly of the medical device 102. As previously stated, the stiffener created by these shelves aids in resisting the enclosure walls from being twisted, warped, pressed inward or outward, or from otherwise being distorted from the original shape.

The portion 230 also includes additional internal features produced by machining. These additional internal features include standoffs 238 that are present in the transitional portion of the bottom wall portion 234 in this example. The standoffs 238 are humps that are directed inward from the boundary wall and edge 236. According to this example, the battery of the medical device 102 is positioned in the lower compartment 206 and the battery fits between the standoffs 238 on opposing sides of the portion 230. The standoffs 238 thereby create a gap between the outer surface of the battery and the walls and edges of the lower compartment 206. Upon joining the portion 202 to the portion 230 to complete the upper and lower compartments 204, 206, the edges are bonded together through a procedure such as laser seam welding. This bonding procedure creates significant heat at the bonding site along the edges, and the gap between the battery and the edges created by the standoffs 238 protect the battery from this heat.

Figure 8:
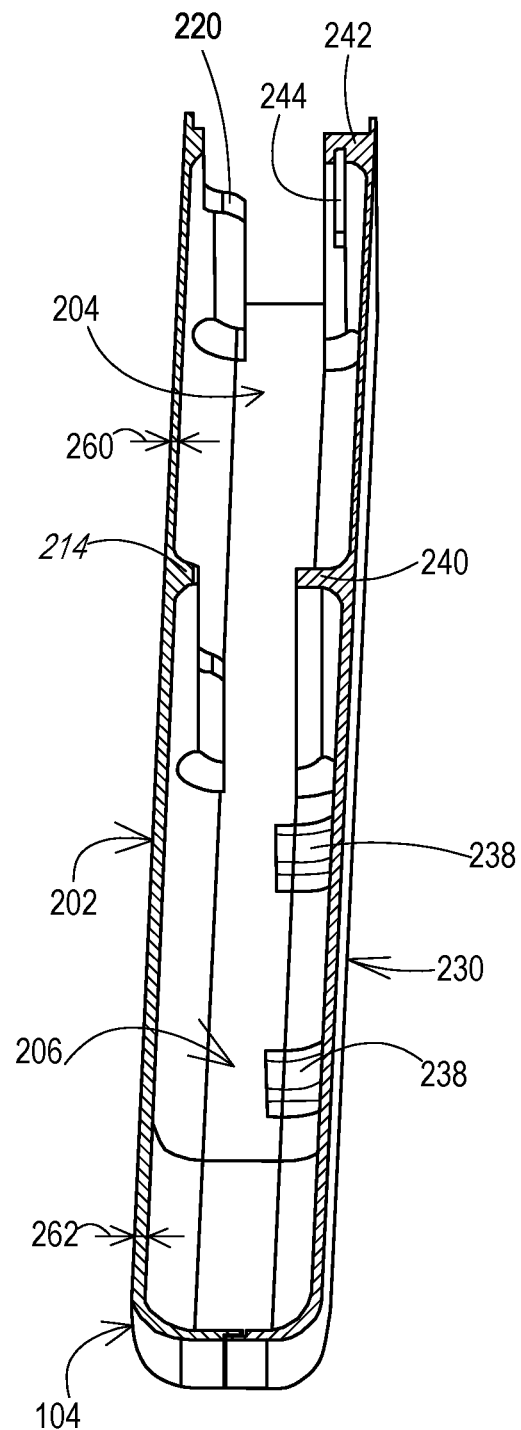
FIG. 8 shows a front cross-sectional view of the enclosure of the implantable medical device.

FIG. 8 shows a front cross-sectional view of the enclosure 104. Internal components contained within the enclosure 104 upon joining the two portions 202 and 230 have been omitted for clarity of illustration. This figure illustrates the completion of the upper compartment 204 bounded by the top shelves 220, 242 and by the intermediate shelves 214, 240. This figure also illustrates the completion of the lower compartment 206 bounded by the intermediate shelves 214, 240 and the bottom transitional wall of the enclosure 104. Other previously discussed internal features are also apparent, including the slot 244 on the bottom surface of the shelf 242 and the standoffs 238 within the lower compartment 206.

Of particular significance, the cross-sectional view of FIG. 8 also illustrates the thickness of the enclosure walls for the compartments 204, 206. As can been seen, the wall portions 208, 232 of the upper compartment 204 are machined to have a first thickness 260. The wall portions 210, 234 of the lower compartment 206 are machined to have a second thickness 262 that is greater than the thickness 260 of the wall portions 208, 232 of the upper compartment 204 in this example.

The differences in thickness may be desirable due to the characteristics and purpose of the internal components contained in each compartment 204 and 206. For instance, a recharge or telemetry coil being located in the upper compartment 204, along with the associated electrical circuitry, will have a higher transfer efficiency with less obstruction between the recharge/telemetry coil and the external coil located outside of the body of the patient 101. Thus, it is beneficial to minimize the thickness 260 although the thickness 260 should be adequate to provide structural integrity for the upper compartment 204 given the surface area of the walls and the relatively low mass of those internal components. For Titanium Grade 5, for instance, as well as other materials a typical range of thickness 260 would be 0.006 inches to 0.012 inches.

In contrast to the internal components of the upper compartment 204, the internal components of the lower compartment 206 of this example are primarily the battery assembly which includes the battery as well as any protective battery coverings. The lower compartment 206 of this example has a volume and surface area that exceeds that of the upper compartment 204 due to the larger external dimensions of the battery, and the battery of this example also has a mass that is greater than that of the internal components within the upper compartment 204. Therefore, the thickness 262 of the lower compartment 206 must be greater than the minimal thickness 260 of the upper compartment 204 in order to establish a structural integrity that resists distortion of the lower compartment 206 due to the mass of the battery and due to the large surface area of the walls. For Titanium Grade 5, for instance, as well as other materials a typical range of thickness 262 would be 0.012 inches to 0.018 inches.

Figure 9:
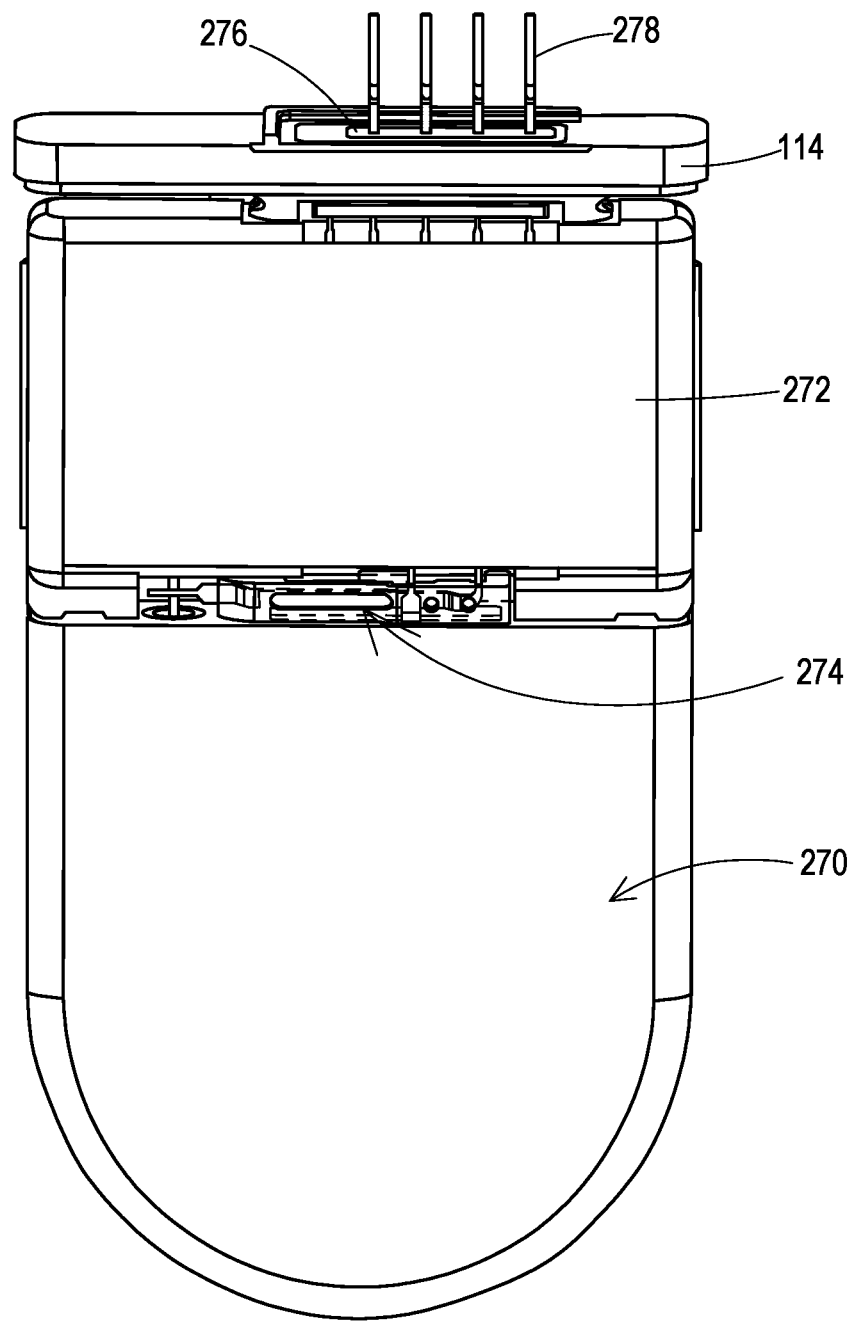
FIG. 9 shows the internal components of the implantable medical device situated as though located within the enclosure.

FIG. 9 shows an example of the internal components that may be included in the medical device 102. The battery 270, which may be an assembly of the battery and any protective covers, is interconnected to electrical circuitry housed within a non-conductive chassis 272 via an assembly of conductors 274 and supporting structures. The assembly of conductors 274 and supporting structures are accommodated by the contoured edges 218 of the enclosure 104 as shown in FIGS. 4 and 5 as well as a small separation between the intermediate shelf 214, 216 of portion 202 and the intermediate shelf 240 of portion 230. The chassis 272, which may be constructed of a rigid non-conductive material such as a polymer, fixes the relative positions of the components of the electrical circuitry including circuit board(s), recharge/telemetry coil(s), and the like.

In this example, the electrical circuitry transfers electrical signals by way of a feedthrough 276 present in the base 114 of the header 106 of the medical device 102. Conductors of the electrical circuitry interconnect with conductive feedthrough pins 278 that pass through the feedthrough 276 and into the internal portion of the header 106 to interconnect with the electrical connectors that are not shown in this view. The feedthrough 276 may be a filtered feedthrough that creates a capacitance between the feedthrough pins 278 and the electrical ground of the electrical circuitry. For instance, the base 114 may be conductive and may be electrically coupled to the electrical ground of the electrical circuitry within the chassis 272 such that the feedthrough capacitance utilizes the base 114 as a grounded node. The electrical interconnection of the conductors to the feedthrough pins 278 may be accommodated by the contoured edge 221 creating additional space as well as a small space between the top shelf 220, 222 and top shelf 242 as shown in FIGS. 6 and 7.

FIG. 10A shows a front cross-sectional view of the medical device 102 including the internal components in the enclosure 104 and in the header 106. Specifically, electrical circuitry 282 is present within the chassis 272 that is present within the upper compartment 204. Electric connectors 284 are present within the header 106 and are electrically connected to the electrical circuitry 282 via the feedthrough pins 278 of FIG. 9. The electrical connectors 284 include a bore 286 that receives the proximal end of the lead 103 so that electrical contacts of the lead 103 reside in the bore 286 and make electrical contact with the electrical connector 284.

FIG. 10A also shows the fit between the chassis 272 and the top shelf 242 where the chassis 272 includes a ridge 280 that is positioned within the slot 244 on the bottom side of the top shelf 242. FIG. 10B shows an enlargement of this area of FIG. 10A to more clearly illustrate the ridge 280 and its positioning within the slot 244. As discussed above, positioning the ridge 280 in the slot 244 provides for alignment and stabilization of the chassis 272 within the upper compartment 204.

This example of FIGS. 1-10B shows various internal features that have been machined into the enclosure 104 of the medical device 102. While these several internal features are shown as being included in the same enclosure 104, it will be appreciated that an enclosure may be constructed that may utilize a different combination and number of these internal features. For instance, some embodiments may include only one of these internal features. Thus, the example of FIGS. 1-10B is for purposes of illustration and is not intended to be limiting.

While embodiments have been particularly shown and described, it will be understood by those skilled in the art that various other changes in the form and details may be made therein without departing from the spirit and scope of the invention.

What is claimed is:

1. An implantable medical device, comprising:
   an enclosure forming a first compartment and a second compartment, the enclosure providing a shelf that separates the first compartment from the second compartment, the first compartment and second compartment each having a wall portion machined as a single wall spanning the first compartment and the second compartment with the shelf machined to extend from the single wall to separate the first compartment from the second compartment;
   electrical circuitry located within the first compartment;
   a battery located within the second compartment, with electrical conductors passing from the battery to the electrical circuitry;
   a first wall portion of the enclosure that provides a surface of the first compartment, the first wall portion having a thickness;
   a second wall portion of the enclosure that provides a surface of the second compartment, the second wall portion having a thickness that is different than the thickness of the first wall portion.

2. The implantable medical device of claim 1, wherein the shelf has a contoured edge.

3. The implantable medical device of claim 1, wherein the thickness of the second wall portion is greater than the thickness of the first wall portion.

4. The implantable medical device of claim 1, wherein the second wall portion defines at least one standoff and wherein the at least one standoff spaces the battery from the second wall portion.

5. An implantable medical device, comprising:
   an enclosure forming a first compartment and a second compartment, the enclosure providing a shelf that separates the first compartment from the second compartment, the first compartment and second compartment each having a wall portion machined as a single wall spanning the first compartment and the second compartment with the shelf machined to extend from the single wall to separate the first compartment from the second compartment;
   electrical circuitry located within the first compartment;
   a battery located within the second compartment, with electrical conductors passing from the battery to the electrical circuitry, wherein the enclosure defines a slot in the interior of the first compartment, the implantable medical device further comprising a chassis positioned within the first compartment and having a ridge, the ridge being positioned within the slot, and wherein the electrical circuitry is located within the chassis.

6. An implantable medical device, comprising:
   an enclosure forming a first compartment and a second compartment, the first compartment and second compartment each having a wall portion machined as a single wall spanning the first compartment and the second compartment;

the wall portion of the first compartment comprising a first wall portion of the enclosure that provides a surface of the first compartment, the first wall portion having a thickness;

the wall portion of the second compartment comprising a second wall portion of the enclosure that provides a surface of the second compartment, the second wall portion having a thickness that is different than the thickness of the first wall portion; and electrical circuitry within the enclosure.

7. The implantable medical device of claim 6, wherein the enclosure comprises a shelf that separates the first compartment from the second compartment.

8. The implantable medical device of claim 6, wherein the electrical circuitry is located within the first compartment, and further comprising a battery that is located within the second compartment with electrical conductors coupling the battery to the electrical circuitry.

9. The implantable medical device of claim 8, wherein the second wall portion defines at least one standoff and wherein the at least one standoff spaces the battery from the second wall portion.

10. The implantable medical device of claim 6, wherein the thickness of the second wall portion is greater than the thickness of the first wall portion.

11. The implantable medical device of claim 6, wherein the enclosure defines a slot in the interior of the first compartment, the implantable medical device further comprising a chassis positioned within the first compartment and having a ridge, the ridge being positioned within the slot, and wherein the electrical circuitry is located within the chassis.

12. An implantable medical device, comprising:
an enclosure forming a wall, the wall defining at least one standoff;
electrical circuitry within the enclosure; and
a battery located within the enclosure and electrically coupled to the circuitry, wherein the at least one standoff spaces the battery from the wall, wherein the enclosure comprises a shelf that separates a first compartment formed by the enclosure from a second compartment formed by the enclosure, and wherein the implantable medical device further comprises:
a first wall portion of the enclosure that provides a surface of the first compartment, the first wall portion having a thickness;
a second wall portion of the enclosure that provides a surface of the second compartment, the second wall portion having a thickness that is different than the thickness of the first wall portion.

13. The implantable medical device of claim 12, wherein the thickness of the second wall portion is greater than the thickness of the first wall portion.

14. The implantable medical device of claim 12, wherein the enclosure defines a slot in the interior of the first compartment, the implantable medical device further comprising a chassis positioned within the first compartment and having a ridge, the ridge being positioned within the slot, and wherein the electrical circuitry is located within the chassis.

15. An implantable medical device, comprising:
an enclosure forming at least a first compartment, the enclosure defining a slot in the interior of the first compartment; and
a chassis positioned within the first compartment and having a ridge, the ridge being positioned within the slot; and
electrical circuitry within the chassis.

16. The implantable medical device of claim 15, wherein the enclosure comprises a shelf that separates the first compartment from a second compartment formed by the enclosure.

17. The implantable medical device of claim 16, further comprising:
a first wall portion of the enclosure that provides a surface of the first compartment, the first wall portion having a thickness;
a second wall portion of the enclosure that provides a surface of the second compartment, the second wall portion having a thickness that is different than the thickness of the first wall portion.

18. The implantable medical device of claim 17, wherein the thickness of the second wall portion is greater than the thickness of the first wall portion.

19. The implantable medical device of claim 17, further comprising a battery located within the second compartment, wherein the second wall portion defines at least one standoff and wherein the at least one standoff spaces the battery from the second wall portion.

20. A method of constructing an enclosure for a medical device, comprising:
machining an enclosure from a material, the machining producing a shelf that separates the enclosure into a first compartment and a second compartment, the first compartment and second compartment each having a wall portion machined as a single wall spanning the first compartment and the second compartment with the shelf machined to extend from the single wall to separate the first compartment from the second compartment;
placing electrical circuitry within the first compartment; and
placing a battery within the second compartment, with electrical conductors passing from the battery to the electrical circuitry,
wherein a first wall portion of the enclosure that provides a surface of the first compartment, the first wall portion having a thickness, and wherein a second wall portion of the enclosure that provides a surface of the second compartment, the second wall portion having a thickness that is different than the thickness of the first wall portion.

21. A method of constructing an enclosure for a medical device, comprising:
machining an enclosure from a material, the machining producing a first compartment and a second compartment, the first compartment and second compartment each having a wall portion machined as a single wall spanning the first compartment and the second compartment where the wall portion of the first compartment comprises a first wall portion of the enclosure provides a surface of the first compartment, the first wall portion having a thickness and where the wall portion of the second compartment comprises a second wall portion of the enclosure provides a surface of the second compartment, the second wall portion having a thickness that is different than the thickness of the first wall portion; and
placing electrical circuitry within the enclosure.

22. A method of constructing an enclosure for a medical device, comprising:
machining an enclosure from a material, the machining producing an enclosure forming a wall, the wall defining at least one standoff;

placing electrical circuitry within the enclosure; and placing a battery within the enclosure and electrically coupled to the circuitry, wherein the at least one stand-off spaces the battery from the wall, wherein a first wall portion of the enclosure that provides a surface of the first compartment, the first wall portion having a thickness and wherein a second wall portion of the enclosure that provides a surface of the second compartment, the second wall portion having a thickness that is different than the thickness of the first wall portion.

23. A method of constructing an enclosure for a medical device, comprising:

machining an enclosure from a material, the machining producing an enclosure forming at least a first compartment, the enclosure defining a slot in the interior of the first compartment;

placing electrical circuitry within a chassis; and placing the chassis within the first compartment, the chassis having a ridge, the ridge being positioned within the slot.

* * * * *